United States Patent [19]
Hofmann

[11] Patent Number: 6,009,345
[45] Date of Patent: Dec. 28, 1999

[54] METHOD AND APPARATUS FOR A COMBINATION OF ELECTROPORATION AND IONTOPHORESIS FOR THE DELIVERY OF DRUGS AND GENES

[75] Inventor: Gunter A. Hofmann, San Diego, Calif.

[73] Assignee: Genetronics, Inc., San Diego, Calif.

[21] Appl. No.: 08/964,436

[22] Filed: Nov. 4, 1997

Related U.S. Application Data

[63] Continuation-in-part of application No. 08/552,200, Nov. 2, 1995, Pat. No. 5,688,233, and a continuation-in-part of application No. 08/310,647, Sep. 22, 1994, Pat. No. 5,464,386, which is a continuation-in-part of application No. 08/219,970, Mar. 30, 1994, Pat. No. 5,462,520, which is a continuation-in-part of application No. 07/931,061, Aug. 17, 1992, Pat. No. 5,318,514.

[51] Int. Cl.⁶ .................................................... A61N 1/30
[52] U.S. Cl. ............................ 604/20; 935/52; 435/173.6
[58] Field of Search ........................... 435/173.6; 935/52; 604/19, 20

[56] References Cited

U.S. PATENT DOCUMENTS

| | | | |
|---|---|---|---|
| 5,019,034 | 5/1991 | Weaver et al. .............................. | 604/20 |
| 5,318,514 | 6/1994 | Hofmann .................................... | 604/20 |
| 5,439,440 | 8/1995 | Hofmann .................................... | 604/20 |
| 5,464,386 | 11/1995 | Hofmann .................................... | 604/20 |
| 5,688,233 | 11/1997 | Hofmann et al. .......................... | 604/20 |

FOREIGN PATENT DOCUMENTS

| | | | |
|---|---|---|---|
| 0 532 451 A1 | 3/1993 | European Pat. Off. ......... | A61N 1/30 |
| 855841 | 5/1940 | France . | |
| WO 96/00111 | 1/1996 | WIPO .............................. | A61N 1/30 |

*Primary Examiner*—Robert L. Nasser
*Attorney, Agent, or Firm*—Baker & Maxham

[57] ABSTRACT

An apparatus for transdermal molecular delivery, comprises a first electrode assembly having an anode and a cathode in closely spaced relation for engaging the stratum corneum through which to apply an electric field, first power supply including a first circuit connected to the first electrode assembly for applying a pulsed electric field of sufficient amplitude to induce pores in the stratum corneum, a second electrode assembly spaced from the first electrode assembly and comprising at least one of an anode and a cathode, second power supply including a second circuit connected to the first electrode assembly and the second electrode assembly for applying a low voltage continuous electric field of a preselected polarity and sufficient amplitude to induce migration of molecules through pores in the stratum corneum.

22 Claims, 4 Drawing Sheets

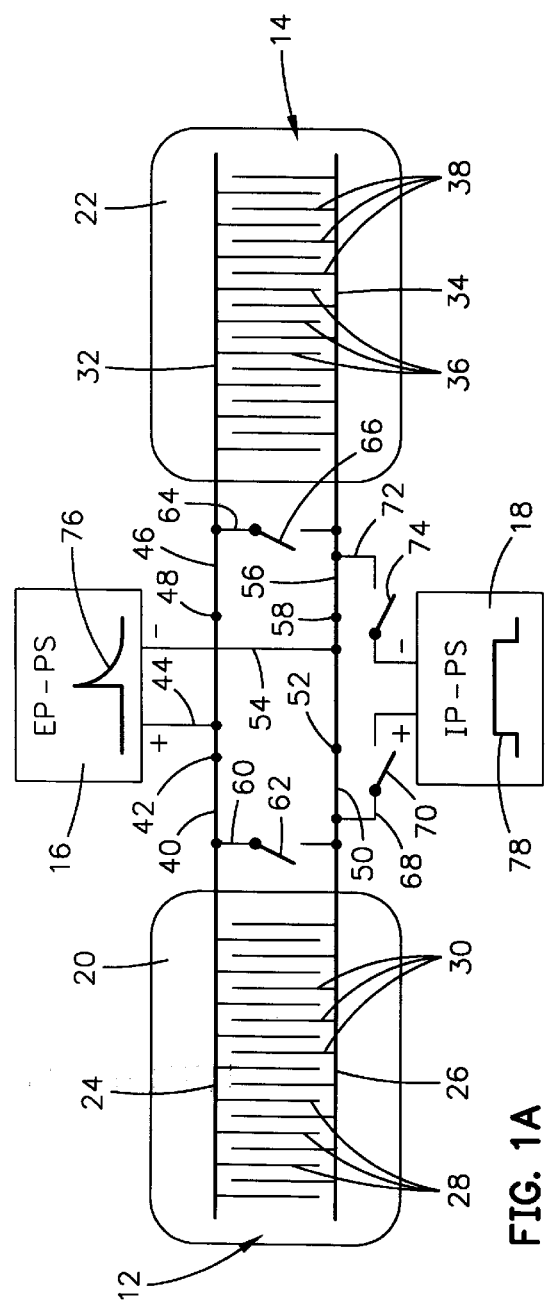
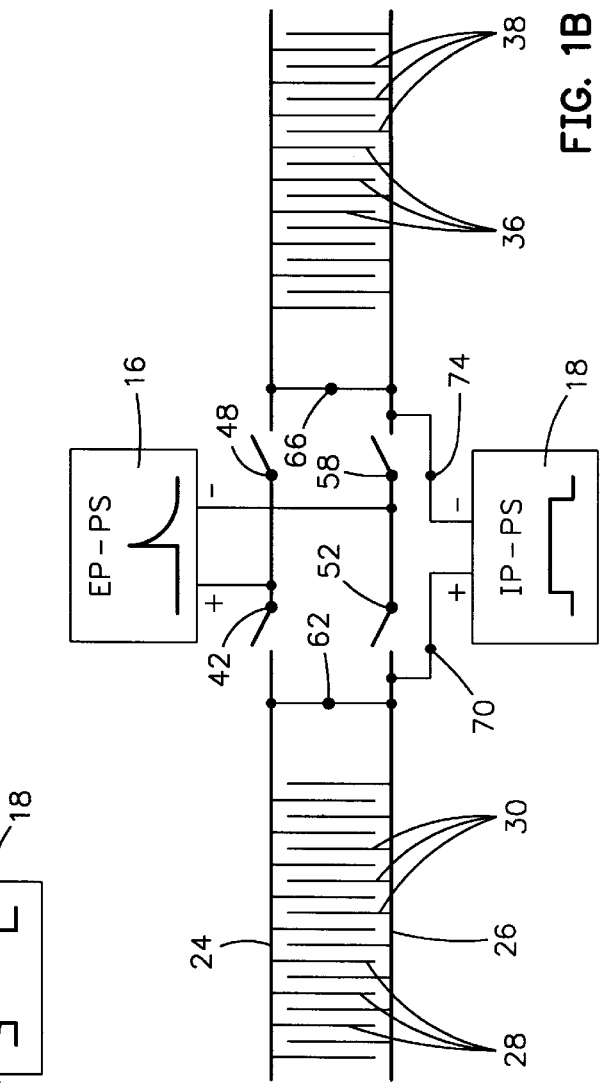
FIG. 1A
FIG. 1B

METHOD AND APPARATUS FOR A COMBINATION OF ELECTROPORATION AND IONTOPHORESIS FOR THE DELIVERY OF DRUGS AND GENES

REFERENCE TO RELATED APPLICATION

The present application is a continuation-in-part of application Ser. No. 08/552,200, entitled "ELECTROINCORPORATION ENHANCED TRANSDERMAL DELIVERY OF MOLECULES", filed Nov. 2, 1995, now U.S. Pat. No. 5,688,233. The present application is a continuation-in-part of application Ser. No. 08/310,647, entitled "TRANSDERMAL DRUG DELIVERY BY ELECTROINCORPORATION OF VESICLES", filed Sept. 22, 1994, now U.S. Pat. No. 5,464,386, which is a continuation-in-part of application Ser. No. 08/219,970, entitled "TRANSSURFACE DRUG DELIVERY BY ELECTROFUSION OF MICROBUBBLES TO THE TISSUE SURFACE", filed Mar. 30, 1994, now U.S. Pat. No. 5,462,520, which is a continuation-in-part of application Ser. No. 07/931,061, filed Aug. 17, 1992, entitled "APPLICATOR FOR THE ELECTROPORATION OF DRUGS AND GENES INTO SURFACE CELLS", now U.S. Pat. No. 5,318,514 dated Jun. 7, 1994.

BACKGROUND OF THE INVENTION

The present invention relates to drug and gene delivery pertains particularly to an apparatus and method combining electroporation and iontophoresis for the transdermal delivery of genes, drugs and other molecules.

The medical community has long sought improved methods of transdermal delivery of medications, drugs and other molecules and fluids without physical penetration or invasion of the tissue surface. In the aforementioned applications there are disclosed apparatus and methods for the transdermal delivery of molecules such as drugs, immunizing agents, and genes into underlying tissue, cells, and to remote tissue.

In the second aforementioned parent application, there are disclosed methods and apparatus for the electroporation of drugs, immunizing agents, and genes into surface cells. In that application, apparatus is disclosed for delivery of a fluid medium carrying preselected molecules to a tissue surface and thereafter applying electrical signals by means of electrodes to the surface tissue. The field is applied at a predetermined strength and duration in order to make the walls of the tissue surface transiently permeable to permit the molecules to pass through the tissue surface into underlying tissue. Further electroporation can enable the molecules to enter preselected cells without damaging them. In another U.S. Pat. No. 5,304,120, entitled ELECTROPORATION METHOD AND APPARATUS FOR INSERTION OF DRUGS AND GENES INTO ENDOTHELIAL CELLS, certain methods and apparatus are disclosed for insertion of drugs and genes into endothelial cells. The teachings of these patents are incorporated herein by reference.

One difficulty with the prior apparatus is that the stratum corneum (SC) which consists of a thin layer of dead cells with a high electrical resistance presents a major obstacle to the administration of drugs and genes transdermally. This layer can be perforated by the administration of short high voltage electrical field pulses, which creates a dielectric breakdown of the stratum corneum forming pores which can allow the passage of molecules However, in order to transport molecules and solutions containing molecules through the pores, a driving force has been found to be needed. This driving force can be provided by any number of mechanisms as discussed in the aforementioned patents including iontophoresis. However the known electroporation apparatus and methods for efficient application of these principles is limited.

Among the prior art relating generally to this field is the Weaver et al. U.S. Pat. No. 5,019,034 entitled "Control of Transport of Molecules Across Tissue Using Electroporation". Weaver seeks an alternative to the traditional syringe and gun injection ot medications. He describes a proposal for using high voltage, short duration electrical pulses on the skin surface to produce electroporation of the tissue to enable drugs and medication to pass into the tissue. However, his disclosed apparatus and methods have limited effectiveness.

The co-pending parent application presents an invention designed to overcome the problems of the prior art by providing means to overcome the resistance to the administration of drugs transdermally presented by the stratum corneum. In accordance with one of the co-pending applications, drugs, immunizing agents, or genes are loaded into vesicles, the vesicles are brought into physical contact with the skin surface and a pulsed electrical field is applied between the vesicles and the tissue by means of electrodes. This forms pores at the interface of the vesicles and the stratum corneum such that the vesicles are pulled through an opening by dielectrophoretic force. While that approach is shown to be successtul to transport effective amounts of molecules of drugs and the like in or into the skin, it requires encapsulation into vesicles.

Electroporation is typically carried out by applying high voltage pulses between a pair of electrodes which are applied to the tissue surface. The voltage that must be applied in proportional to the distance between the electrodes. When the space between the electrodes is too great, the generated electric field penetrates deep into the tissue where it causes unpleasant nerve and muscle reaction.

While electroporation provides new pathways through the stratum corneum for passages of molecules, it does not provide a needed driving force. It is desirable that electroporation be combined with techniques for providing a driving force such as electro-incorporation, pressure or concentration gradient, sonophoresis or iontophoresis.

It is known that iontophoresis wherein low voltage is applied between widely spaced electrodes for a long period of time can transport charged molecules through existing pathways such as hair follicles and sweat glands. However, the volumes of molecules transported is very small, and insufficient for many applications. Combining electroporation and iontophoresis can increase the amount transported initially while the created pathways are open. However, the paths created by the electroporation stay open for a short period ot time and then close.

It is desirable that a simpler apparatus and method be available to combine both electroporation and iontophoresis without the unpleasant side effects for transport molecules through or into the stratum corneum.

SUMMARY AND OBJECTS OF THE INVENTION

It is the primary object of the present invention to provide an improved method and apparatus for combining electroporation and iontophoresis without the unpleasant side effects for transport molecules through or into the stratum corneum.

In accordance with the primary aspect of the present invention, drugs or genes are brought into physical contact with the skin surface, an electrode is contacted with the surface and a pulsed electrical field is applied to the skin surface by means of electrodes. This forms pores in the stratum corneum (SC), and pressure is applied to the skin surface forcing drugs or genes or immunizing agent through the SC into the skin.

BRIEF DESCRIPTION OF THE DRAWINGS

The above and other objects and advantages of the present invention will be appreciated from the following specification when read in conjunction with the accompanying drawings wherein:

FIG. 1a is a schematic illustration of an apparatus in accordance with an exemplary embodiment of the present invention shown in the electroporation mode of operation;

FIG. 1b is a schematic illustration of an apparatus in accordance with an exemplary embodiment of the present invention shown in the iontophoresis mode of operation;

DETAILED DESCRIPTION OF THE PREFERRED EMBODIMENTS

Figure 2:
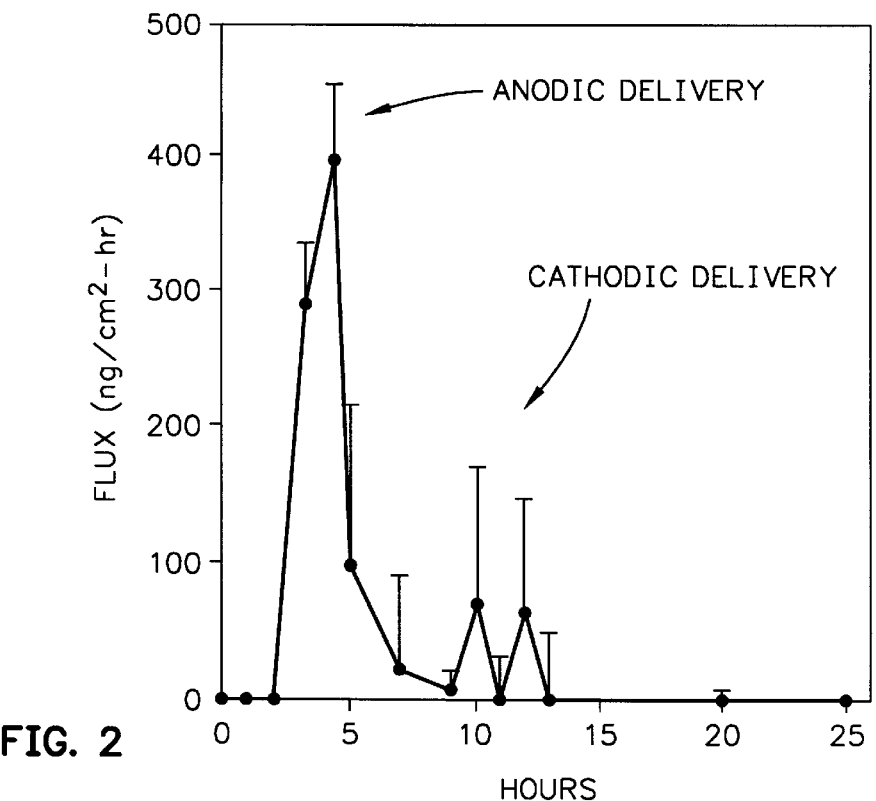
FIG. 2 is a graph showing a comparison of the relative efficiency of sCT through human skin via anodic versus cathodic electrode.

The present invention was devised to overcome the problem presented by the resistance of the stratum corneum to the transport of genes and drugs. The invention takes advantage of dielectric breakdown of the stratum corneum (SC) to transfer molecules such as drugs and genes across the SC surface into the underlying tissue and possibly into the blood stream. It also provides a system that reduces the unpleasant side effects of the high voltage necessary for SC breakdown. A force or pressure such as iontophoresis is preferably applied to the molecules after the poration to increase the rate of transport through the SC or tissue. When desirable, subsequent electroporation may be applied to improve the uptake of drugs, genes, DNA or the like, into cells in the living tissue of humans and other living organism.

Electroporation involves the transient formation of pores in tissue or cell membranes utilizing one or more short pulses of high-voltage electric field. Once these pores are formed in the tissue, fluids containing drugs, DNA and other molecules can pass through the SC into and through the tissue. Once in the tissue, pores in cell membranes enable DNA and other molecules to enter the cells through these pores in the cell walls. Thereafter, they stay encapsulated in the cell and the cell walls reseal themselves. The DNA or other gene or drug can then act within the cell to alter the cell properties. Fluids can also be more easily withdrawn from the tissue with electroporation.

It is known that iontophoresis can be used as a driving force to force molecules across tissue surfaces. I have found that this force or pressure may be applied during the application of electrical pulses for poration or up to one minute after the application of the electrical pulses. Transdermal resistance measurements has shown that the skin remains in a low resistance state for up to one minute after the application of electrical pulses. Thus, the fluid can also be applied to the tissue surface up to one minute after the application of the electrical pulses.

The present invention was devised to enhance the introduction of molecules across skin surfaces. When dealing with the Stratum Corneum (SC) the flux can be increased at periodical intervals to maintain poration and the iontophoresis force applied until the desired amount of the molecules are transported through the stratum corneum.

Referring to FIG. 1 of the drawing, an apparatus in accordance with the invention is schematically illustrated and designated generally by the numeral 10. The apparatus comprises a pair of electrode assemblies 12 and 14 connected by an electrical circuit to both an electroporation power supply 16, and an iontophoresis power supply 18. This power supply may in fact be a single power unit with circuitry for the two modes of operation. The electrode assemblies each comprise a support member 20 and 22 on which is mounted an array of electrodes through which circuits can be switched to selectively apply electroporation or iontophoresis to a body of a mammal. In the illustrated embodiment, the support member 20 and 22 are illustrated as patches that may be detachably applied directly to the SC or skin surface. However, the support member may be any suitable structure as will be subsequently discussed.

The electrode assembly 12 comprises a pair or parallel spaced apart conductors 24 and 26 mounted on a planar surface of support member 20 and each having a plurality of closely spaced electrodes extending outward therefrom toward the other of the conductors. A plurality of electrodes 28 extend outward from right angles to the conductor 24 toward the conductor 26. A plurality of electrodes 30 extend outward at right angles from the conductor 26 toward the conductor 24. These form alternate electrodes closely spaced along the surface of the support member 20. In a preferred embodiment the electrodes are closely spaced on the order of about 0.2 mm to about 0.5 mm. These electrodes are also very small such as on the order of about 0.2 to 1 mm in width. These form what has been termed a "meander electrode". The advantage of these closely spaced electrodes is that high voltages can be applied to the tissue between the electrodes without inducing high voltage deeply in underlying tissue.

The electrode 22 is similarly constructed of a pair of parallel conductors 32 and 34 with a plurality of electrodes 36 extending outward from the conductor 34 and a similar plurality of electrodes 38 extending outward from the conductor 34 toward a conductor 32.

The support members 20 and 22 for the electrode assemblies may be any suitable support member such as a flexible patch that may be taped to a users skill or it may be the surface of another form of manipulator which can be manually positioned and manipulated. For example, they may be mounted on hand-held applicators and forceps or other clamps as will be subsequently described.

The conductor 24 and electrodes 28 of the electrode assembly 12 is connected by conductor 40 having a switch 42 to conductor 44 to the electroporation power supply 16. Similarly, the conductor 32 of the assembly 14 is connected by a conductor 46 and switch 48 to the conductor 44 at the positive side of the electroporation power supply 16.

The conductor 26 of the electrode assembly 12 is connected by way of conductor 50 with a switch 52 to conductor 54 to the electroporation power supply 16. Similarly, the conductor 34 of the electrode assembly 14 and the electrodes 38 are connected by way of a conductor 56 and switch 58 to the conductor 54 which connects to the negative side of the electroporation power supply 16. A conductor 60 with switch 62 connects between the conductors 40 and 50. Similarly, a conductor 64 with a switch 66 connects between the conductors 46 and 56.

A conductor 68 with switch 70 connects the conductor 50 to the positive side of the iontophoresis power supply 18. A conductor 72 with a switch 74 connects the conductor 56 to the negative side of the iontophoresis power supply 18. With this arrangement the switches are set as in FIG. 1 so that electrodes 28 of assembly 12 and electrodes 36 of assembly 14 are connected to the positive side of the electroporation power supply and electrodes 30 of electrode assembly 12 and electrodes 38 of assembly 14 are connected to the negative side of the electroporation power supply. With this arrangement the electroporation power supply can apply high voltage pulses represented by the curve 76 to the electrode assemblies with the closely spaced electrodes supplying the fields to tissue surface without underlying discomfort.

As soon as a predetermined electroporation of the stratum corneum has been completed, the molecules to be passed through the stratum corneum, if not already in place. are placed in contact with the SC underneath one or the other of the electrode assemblies and the electroporation power supply 16 is deactivated and the iontophoresis power supply 18 is activated. The iontophoresis power is a lower longer power duration power as represented by the curve 78. This occurs as shown in FIG. 2 by opening switches 42 and 48, closing switches 62 and 66, opening switches 50 and 58, and closing switches 70 and 74. The iontophoresis power supply then acts to supply the force necessary to transport the molecules of genes or drugs across the stratum corneum into the underlying tissue. As previouslly pointed out, the openings in the stratum corneum provided by the electroporation last for about 1–2 minutes following the electroporation. Should this be insufficient to pass the required quantity of molecules through the stratum corneum, the procedure can be repeated by again electroporating and thereafter applying iontophoresis.

Where the volume of molecules to be transported is sufficiently large that quite a number of repeats of electroporation is necessary, an automatic timing function can be built into the electroporation and iontophoresis system, such that alternate electroporation and iontophoresis can be applied for a predetermined length of time until the necessary volume of molecules has been transported. The electroporation can be carried out by a sophisticated electroporation system having programmable power sequence and duration programmed in. A suitable system is disclosed in my co-pending application Ser. No. 08/709,615 filed Sep. 9, 1996, entitled ELECTROPORATION EMPLOYING USER-CONFIGURED PULSING SCHEME, which is incorporated herein by reference as though fully set forth.

Broadly, that invention concerns an electroporation method and apparatus for generating and applying an electric field according to a user-specified pulsing scheme. One example of such a pulsing scheme includes a low voltage pulse of a first duration immediately followed by a high voltage of a second duration, immediately followed by a low voltage of a third duration. The invention provides the low voltage electroporation field to accumulate molecules at the surface of a cell, the appropriately high voltage field to create an opening in the cell, and the final low voltage field to move the molecule into the cell.

In the present invention, the high voltage serves to create pores in the stratum corneum, the low voltage serves to provide the iontophoretic driving force. Appropriate switch positions need to be assured between the different pulses.

The molecules may be genes or drugs such as DNA, portions of DNA, chemical agents or any other molecule. The molecules are placed in close proximity to the cells, either in the interstitial tissue surrounding the cells or in a fluid medium containing the cells.

Accordingly, that invention concerns a method of generating and applying an electric field according to a user-selected pulsing scheme to more efficiently introduce molecules into cells and minimize damage to cellular tissue.

Another aspect of that invention concerns an apparatus comprising an electrical pulse generator to generate and apply such a pulsing scheme. One embodiment of such an apparatus utilizes the following components. First and second power supplies provide first and second respective output voltages. A transformer, with primary and secondary windings, has a pair of output terminals coupled to the secondary windings. A first switch, responsive to a first gating signal, applies the first output voltage to the primary winding. A second switch. responsive to a second gating signal, applies the second voltage directly to the output terminals. A controller receives user specification of an output pulse pattern, and provides the first and second gating signals to generate the specified output pulse pattern at the output terminals.

As can be seen from FIG. 1a and FIG. 1b, the FIG. 1 embodiment, the electrode assemblies 12 and 14 are each made up of opposing electrodes functioning in the electroporation mode. When the system is converted to the iontophoresis mode. as will be seen in FIG. 1b, the electrodes of each electrode assembly are then connected in parallel such that each assembly becomes an electrode, thus the assembly 12 becomes a single electrode and the assembly becomes a single electrode in the iontophoresis mode. Also in this mode. the inventor has found that for certain molecules the delivery or transport under the anode is considerably greater than that under the cathode.

Since skin can undergo charge reversal at low pH (which would change the direction of electroosmotic flow) an initial experiment investigated the iontophoretic delivery of Salmon Calcitonin (sCT) under both anode and cathode to ensure that optimal delivery is achieved under anode. It was seen that there was no permeation across human epidermis for the first two hours when no current was applied. Permeation started when current was applied to sCT solution via anode from the second to fourth hour. The skin was then allowed to recover and current was reapplied at the tenth to twelfth hour, but under cathode this time. The results confirm that optimal delivery is obtained under the anode.

FIG. 2 is a graph illustrating the comparison of relative efficiency of sCT delivery through human skin via anodic vs. cathodic electrodes. In this experiment, a donor concentration of 50 $\mu$g per ml of sCT spiked with 0.25 $\mu$ Ci-$\mu$l of I-sCT was used. The amount of sCT delivered to the skin preparation was determined by sampling from the receptor side over time, counting the amount of labelled sCT in a scintillation counter. Note the rapid rise of sCT being delivered through the skin membrane after onset of iontophoresis, and the rapid fall of sCT levels after iontophoresis stopped. This indicates that sCT moves rapidly through the skin without pooling and behaves as in a near ideal substance for iontophoresis. This experiment showed that optimum delivery is achieved under the anode form for certain charge molecules.

Figure 3:
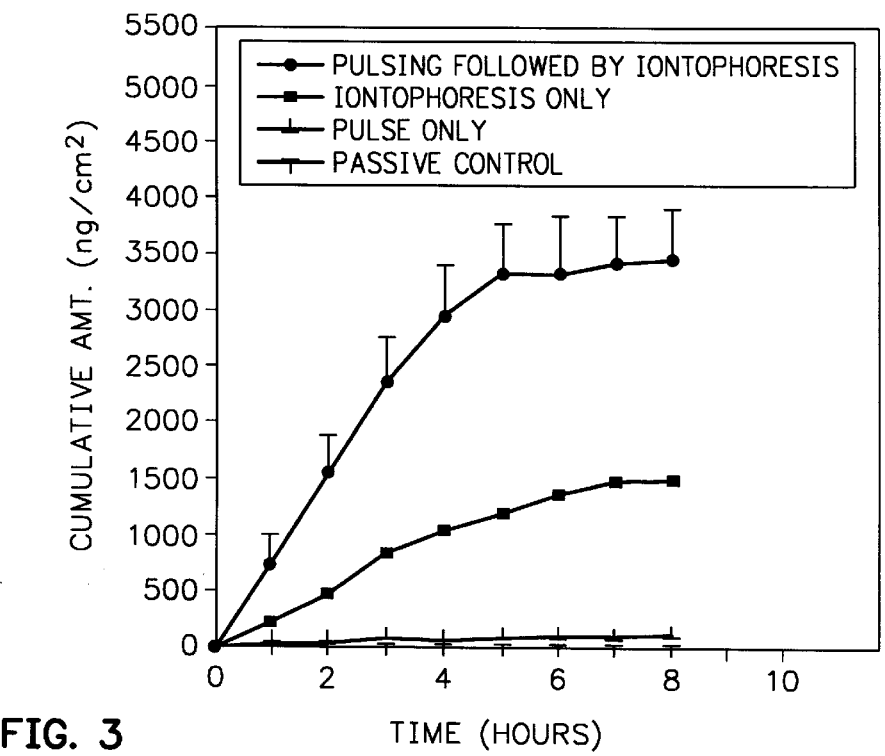
FIG. 3 is a graph showing a comparison of the relative efficiency of electrical enhancement of transdermal sCT delivery.

Referring to FIG. 3, the results of several subsequent studies on a comparison of various modes of electrical enhancement are combined into the FIG. 3 for comparison As can be seen, there was no passive permeation in the absence of electrical enhancement ot sCT across human epidermal membrane. Iontophoresis applied for four hours resulted in a state flux of about 200 ng/cm$^2$/hr. In contrast, if electroporation pulses were given prior to iontophoresis, a flux of about 800 ng/cm$^2$/hr was achieved. Assuming a 5 cm$^2$ patch, this allows for a total delivery of 4 $\mu$g/hour so that the therapeutic daily dose of 100 I.U.'s of sCT (about 20 $\mu$gm) could be delivered in five hours with this protocol. The concentration of sCT used in this experiment was only 50 $\mu$ per ml. If this is increased to 250 $\mu$g/ml and a linear relationship is assumed, then a therapeutic dose can be delivery in one hour.

In a comparison study of the efficiency of electrical enhancement of transdermal sCT delivery, iontophoresis and electroporation were compared alone, and together, to asses their effect on transdermal sCT delivery. Conditions of the study were similar to those above, except that samples were collected every hour and total accumulated levels of $^{125}$I-sCT were measured. These results shown in FIG. 4 clearly show a synergistic effect of electroporation combined with iontophoresis. As stated in the text, an increase from 200 ng/cm$^2$/hr to about 800 ng/cm$^2$/hr was achieved when the skin was pre-pulsed.

The electrode assemblies, in accordance with the present invention, can be mounted in or on any number of different carriers to suit the particular application. For example. the carriers may be patches which are taped to the skin of the subject, or mechanical devices for hand or remote machine manipulation.

Figure 4:
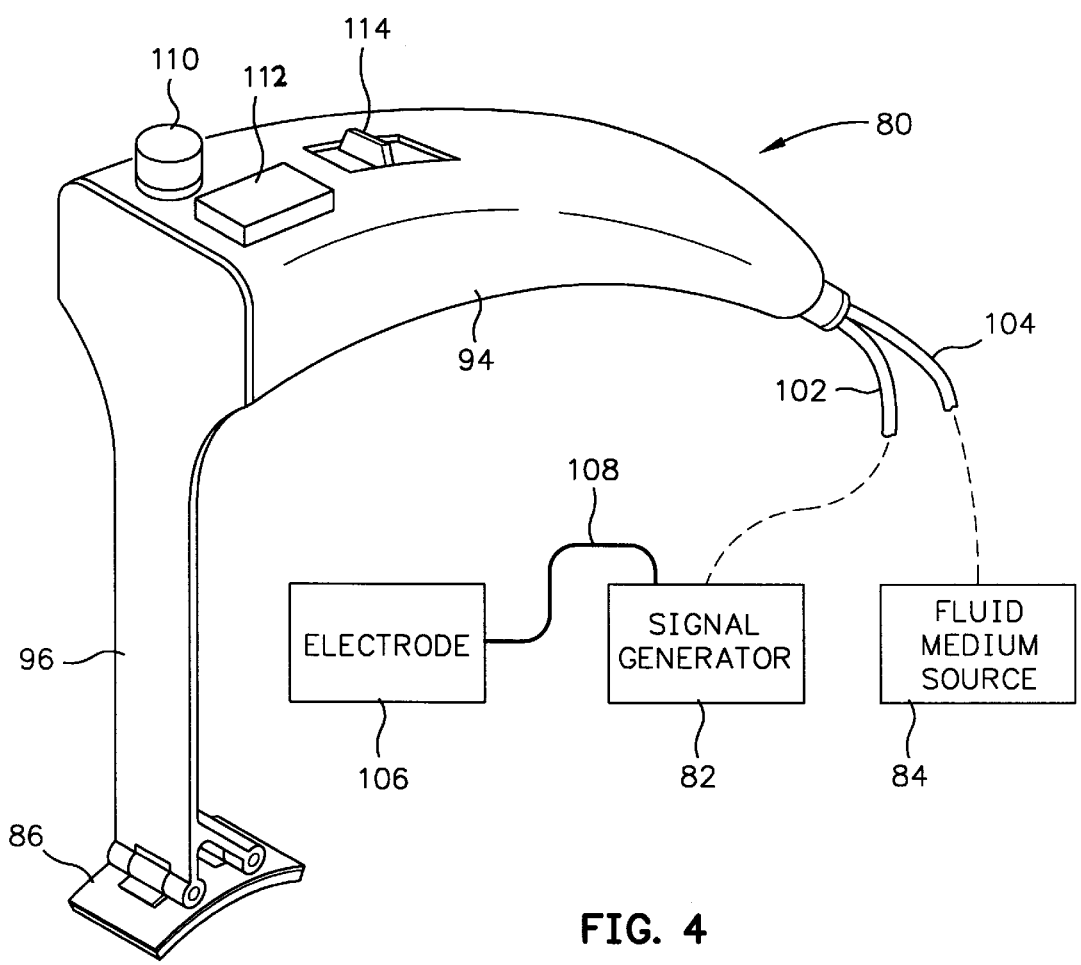
FIG. 4 is a perspective view of a system in accordance with the invention having a hand applicator, clamp or calipers type electrode apparatus for applying the electric fields and pressure.
Figure 5:
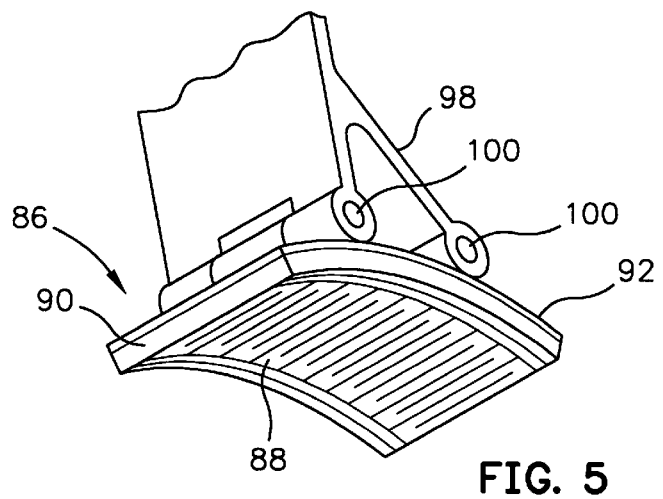
FIG. 5 is an enlarged view of the head assembly of the FIG. 4.

Alternate carrier assemblies or manipulating implement for the electrodes of the present invention may take on any number of suitable forms. Referring to FIG. 4, an exemplary embodiment of a hand manipulated carrier is illustrated in an apparatus in accordance with the invention and which may be utilized as the apparatus and in carrying out the process of the present invention. The device comprises a manually positionable applicator designated generally by the numeral 80 which is connected to a signal generator 82 and a pressurized fluid medium source 84 which preferably includes a pump. The applicator 80 has a head assembly 86 which engages and applies a fluid containing molecules of genes. immunizing agents or drugs and vesicles, and electrical pulses to a preselected surface tissue region of a patient. Further details of the head assembly are illustrated in FIG. 5.

The head assembly comprises an electrode assembly 88 which are like those of FIG. 1 and which is carried or mounted on a carrier or applicator such as an open pore foam elastomer 90 carried by flexible semirigid or firm dielectric planar support member 92. Adjacent parallel segments of conductors serve as opposed electrodes for application of the electroporation electric field to the tissue surface. The electrodes are preferably small and closely spaced, such as about 0.2 mm to 1 mm width at about 0.2 mm spacing. The electrode assembly 88 is preferably switchable like those of FIG. 1 to provide the electroporation and then switchable to serve as one of the iontophoresis electrodes, preferably the anode. Both meander electrodes as described in FIG. 1 can be mounted on the head assembly 86. The meander electrodes can have other geometries (e.g. circular), as long as there is an equidistant narrow gap between the electrodes.

The applicator 80 (FIG. 4) further includes a handle portion 94 and an arm portion 96 on which is mounted the head assembly 86. The head assembly 86 is connected to a Y-shaped distal end 98 by means of a pair of pins 100. These pins enable the head to flex and conform to the curvature of the skin surface.

The terminal ends of the conductors or electrodes ot array 88 are connected to the signal generator 82 by way of an electrical cable 102. A fluid medium carrying the molecules or drugs and vesicles is supplied from the fluid medium source 84, which may include a suitable motorized pump or pressure source, not shown. The fluid medium source 84 is coupled to the elastomer foam 90 by flexible tube 104 which extends to the applicator 80 and to the foam applicator. A second electrode assembly 106 is connected by a cable 108 to the signal generator 82 for application of the iontophoresis.

An actuator button 110 on the handle 94 of the applicator may be depressed to activate a valve (not shown) and deliver a suitable quantity of the fluid medium to the foam elastomer 90. The elastomer 90 provides a sponge-like substrate for holding a predetermined quantity of the fluid medium for contact with the SC or tissue surface.

An actuator button 112 provides the means for actuation of the circuit for electroporation phase or mode. This may be a push button since the duration of the application of signals for electroporation is short. An actuator switch 114 actuates the circuit for the iontophoresis phase. This is illustrated as a slide button for movement to and from on and off positions due to the longer duration of activation required.

The molecules to be delivered are brought into contact with the tissue surface or stratum corneum of a skin layer by suitable means and are positioned between an assembly of multiple pairs of closely spaced electrodes. This can be carried out by the apparatus of FIG. 4, wherein a fluid carry the molecules and applied by the sponge 90 would be positioned between the electrode assembly 88 on the surface of the applicator and the SC or tissue surface.

Thereafter, a short voltage pulse is applied between the electrodes so that the electric fields of sufficient amplitude are generated to induce dielectric breakdown forming pores in the stratum corneum. A suitable force such as iontophoresis is then applied to the solution containing the molecules to force the molecules to pass through the pores into the underlying tissues. The electric field is preferably applied so that useful electric field lines are perpendicular to the tissue surface or stratum corneum surface. Typical electrical parameters for the stratum corneum are a field strength of 20 to about 60 kV/cm, which can be generated with moderate voltages of 20 to 120 volts with a pulse length of 10 micro-seconds ($\mu$sec) to 100 milliseconds (msec). This electric field induces a dielectric breakdown and pores in the stratum corneum and the molecules can pass through the pores in the SC. Other tissue surfaces will typically require less field strength.

Figure 6:
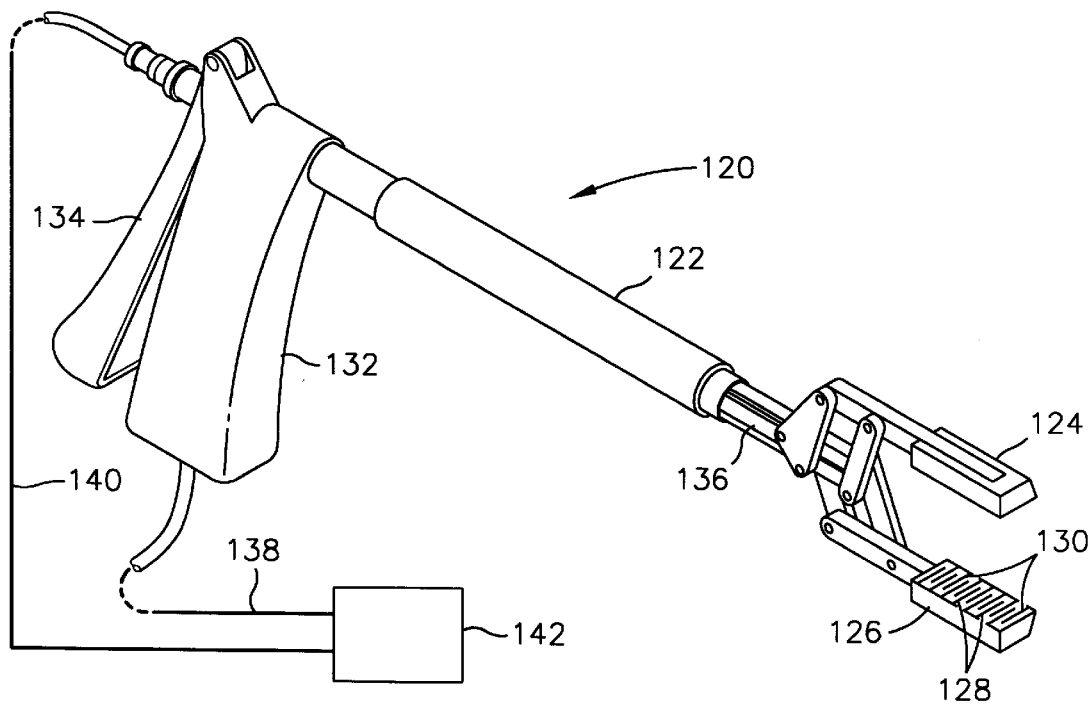
FIG. 6 is a perspective view of a clamp or calipers type electrode apparatus illustrating the calipers in the open position for applying the electric fields and pressure.

Referring to FIG. 6 another type apparatus that may be utilized for carrying out the present invention is illustrated and designated generally by the numeral 120. This device comprises a calipers or forceps device which comprises a body or support member 122 having a pair of electrodes 124 and 126 mounted on an insulated linkage of the distal end thereof. The electrode 126 is constructed as an assembly of multiple small closely spaced opposed electrodes 128 and 130 as in the prior embodiments. A pistol grip handle 132 is mounted on a proximal end of the elongated tubular support member 122 for enabling ease of manipulation of same. The electrodes 124 and 126 are mounted on a moveable linkage so that the electrodes are moveable toward and away from one another like the jaws of a clamp.

A movable handle or grip 134 is pivotally mounted at an upper end to grip 132 and connects through a moveable or actuating link 136 to the electrode links controlling the spacing between them. The electrodes 124 and 126 may be biased by spring means (not shown) acting between grip 132 and actuating handle 134 to either the closed or the open or outermost position. In the present apparatus it is preferable that the electrode jaws be biased to the closed position during the application of the electrical fields. The electrodes 124 and 126 are connected through conductors in cables 138 and 140 to suitable power and pulse generator 142. The power generator 142 is designed to have a circuit as previously described to apply pulsed voltage for electroporation to the closely spaced electrodes 128 and 130 and thereafter to apply a substantially constant voltage to the electrodes 124 and 126 for the iontophoresis phase. The illustrated apparatus 120 is designed for use with a laparoscope for use on the interior of the human or animal body.

In operation, a unit as above described is selected and a selected tissue to be treated is selected and a solution containing molecules to be delivered is applied to the surface of the tissue either before or after electroporation. The tissue is then placed and gripped between the electrode jaws with electrode assembly 126 applied to the area to be electroporated. A signal proportionate to the distance between the electrodes is generated and either manually or electronically entered into the pulse generator 142 so that it generates a pulse proportional to the desired field and applies it to the electrodes 128 and 130. The pulse generator connected to the electrodes is then operated by a trigger switch at the unit, a foot switch, or a switch on the instrument panel for repeatedly applying pulses to the electrodes for generating electric fields of a predetermined amplitude and duration in the tissue between the electrodes. Pores opened up in the tissue surface allow the solution of molecules to enter the tissue aided by the pressure of the electrodes. The power supply is then operated in the iontophoresis mode to generate the necessary force to the molecules to move them through the SC into the underlying tissue.

The electric fields for electroporation are generated by applying a predetermined electric signal to electrodes 128 and 130 of the device. The parameters of the signal are selected so that the surface tissue between the electrodes is subjected to short pulses of high intensity electric fields sufficient to cause electroporation of the tissue between the electrodes. The voltage is adjusted accurately so that the generated field has the desired, optimal amplitude. These fields make the walls of the tissue transiently permeable to permit the molecules to enter the tissue. The permeability results from the temporary formation of pores in the tissue walls which are large enough to permit migration of the molecules through the tissue walls.

The invention can also be carried out by other types of instruments including a catheter type apparatus and methods disclosed in the aforementioned U.S. Ser. No. 07/907,322 which is incorporated herein by reference as though fully set forth. This provides a more convenient apparatus for the delivery of drugs and genes across tissue surfaces and membranes such as in body cavities. The driving force in this catheter arrangement can be applied by the pressure of the delivery fluid for the initial passage through the SC and thereafter iontophoresis applied to transport the molecules further into selected tissue. Other forms of a delivery system could be utilized, such as a small system strapped to the arm or other body part or momentarily connected, containing a rechargeable battery-powered pulse power supply with a reservoir containing fluid containing the drug or other molecules. The fluid could also contain vesicles in suspension with the drug or molecules encapsulated. The applicator would have the basic components as the device in FIG. 4 such that by pushing one button, a preselected amount of solution of molecules or vesicles is delivered to the skin between the electrodes. The solution is are pressed against the skin for good mechanical contact and to apply a driving force. Activating another button or switch delivers an electrical pulse to the electrodes which delivers the molecules through the stratum corneum.

A special patch can also be applied to spaced areas of the tissue surface. The solution can be contained in the patch which also contains the electrode structure to create the electric field. The electrode structure can be similar to that of FIGS. 1 and 2 and inside or on a surface of the patch, the electrode structure is connected to two conductors outside the patch so that a pulse generator can be connected momentarily to these outside electrodes to provide a voltage pulse. The patch is preferably provided with an adhesive border to adhere it to the skin or tissue. It is also preferably provided with a protective cover which can be peeled off before adhering the patch to the skin or tissue. A pressure can be applied mechanically by pressing on the patch with any suitable means for applying a reasonably uniform pressure over the desired area.

If the drug is to be transported into the cells, a second pulse after allowing appropriate diffusion time, is applied to open up pores in the cells. This allows the cells to take up the drug or molecules by electroporation.

While I have illustrated and described my invention by means of specific embodiments, it is to be understood that numerous changes and modifications may be made therein without departing from the spirit and scope of the invention as defined in the appended claims.

I claim:

1. An apparatus for transdermal molecular delivery, comprising:
    a first electrode assembly having an anode and a cathode in closely spaced relation for engaging the stratum corneum through which to apply an electric field;
    a first power supply including a first circuit connected to said first electrode assembly for applying a pulsed electric field of sufficient amplitude to induce pores in the stratum corneum;
    a second electrode assembly spaced from said first electrode assembly and comprising at least one of an anode and a cathode; and
    a second power supply including a second circuit connected to said first electrode assembly and said second electrode assembly for applying a low voltage continuous electric field of a preselected polarity and sufficient amplitude to induce migration of molecules through pores in the stratum corneum.

2. An apparatus according to claim 1 wherein at least one of said first electrode assembly and said second electrode assembly is a meander array of alternating anodes and cathodes.

3. An apparatus according to claim 1 wherein both said first electrode assembly and said second electrode assembly are each a meander array of alternating anodes and cathodes.

4. An apparatus according to claim 3 wherein said anode and said cathode of each array are connected in parallel when connected to said second power supply.

5. An apparatus according to claim 4 wherein said electrode assemblies are mounted on a carrier for hand manipulation.

6. An apparatus according to claim 5 wherein said carrier is a pair of arms moveable toward and away from one another and an electrode assembly is mounted on each arm.

7. An apparatus according to claim 5 wherein said carrier for at least one of said electrode assemblies is a tape.

8. An apparatus according to claim 5 wherein at least one of said electrode assemblies includes an electrode that is porous so that a solution of moledules can pass therethrough.

9. An apparatus according to claim 8 wherein said porous electrode is the anode.

10. An apparatus according to claim 1 wherein said electrode assemblies are mounted on a pair of forceps and an electrode assembly is mounted on each jaw of the forceps and said electrode assemblies each comprise a plurality of closely spaced electrodes adapted to be applied to the surface of the stratum corneum and the pulsed electric field is applied as pulses of from 10 to several hundred volts with a pulse length of between 10 $\mu$sec to 100 msec.

11. An apparatus according to claim 1 wherein:
  at least one of said first electrode assembly and said second electrode assembly includes a planar rectangular support surface;
  a pair of conductors are mounted in spaced parallel relation on said support surface; and
  a plurality of electrodes extend alternately from each conductor towards the other conductor.

12. An apparatus according to claim 11 wherein said electrodes are alternately anodes and cathodes and are spaced 0.2 mm apart.

13. An apparatus for transporting molecules across a stratum corneum, comprising:
  a first electrode assembly having an anode and a cathode in closely spaced relation for engaging the stratum corneum through which to apply an electric field;
  a first power supply including a first circuit connected to said first electrode assembly for applying a pulsed electric field of sufficient amplitude to induce pores in the stratum corneum;
  a second electrode assembly spaced from said first electrode assembly and comprising at least one of an anode and a cathode;
  a second power supply including a second circuit connected to said first electrode assembly and said second electrode assembly for applying a low voltage continuous electric field of a preselected polarity and sufficient amplitude to induce migration of molecules through pores in the stratum corneum.

14. An apparatus according to claim 13 wherein at least one of said first electrode assembly and said second electrode assembly is a meander array of alternating anodes and cathodes.

15. An apparatus according to claim 14 wherein both said first electrode assembly and said second electrode assembly are each a meander assembly of alternating anodes and cathodes.

16. An apparatus according to claim 15 wherein said anode and said cathode of each assembly are connected in parallel when connected to said second power supply.

17. An apparatus according to claim 16 wherein said first electrode assembly and said second electrode assembly are mounted on a pair of arms moveable toward and away from one another.

18. An apparatus according to claim 17 wherein said carrier for said electrode assemblies is a pair of forceps and an electrode array is mounted on each jaw of the forceps said electrode assemblies each comprise a plurality of closely spaced electrodes adapted to be applied to the surface of the stratum corneum and the pulsed electric field is applied as pulses of from 10 to several hundred volts with a pulse length of between 10 $\mu$sec to 100 msec.

19. An apparatus according to claim 16 wherein said anode is porous so that a solution of molecules can pass therethrough.

20. A method for transdermal molecular delivery, comprising:
  providing a first electrode assembly having an anode and a cathode in closely spaced relation;
  engaging the stratum corneum with said first electrode assembly;
  providing first power supply means including a first circuit connected to said first electrode assembly;
  applying a pulsed electric field via said first electrode assembly of sufficient amplitude to induce pores in the stratum corneum;
  providing a second electrode assembly spaced from said first electrode assembly and comprising at least one of an anode and a cathode;
  providing second power supply means including a second circuit connected to said first electrode assembly and said second electrode assembly; and
  applying a low voltage continuous electric field to said electrode assemblies of a preselected polarity and sufficient amplitude to induce migration of molecules through pores in the stratum corneum.

21. A method apparatus according to claim 20 wherein the steps of providing said first electrode assembly and said second electrode assembly includes providing each as a meander assembly of alternating anodes and cathodes.

22. A method apparatus according to claim 21 wherein the step of applying a low voltage continuous field includes connecting said anode and said cathode of each assembly in parallel to said second power supply.

* * * * *